United States Patent [19]

Sherry et al.

[11] Patent Number: 5,342,606

[45] Date of Patent: * Aug. 30, 1994

[54] POLYAZAMACROCYCLIC COMPOUNDS FOR COMPLEXATION OF METAL IONS

[75] Inventors: A. Dean Sherry, Dallas; Istvan Lazar, Richardson, both of Tex.; Erno Brucher, Debrecen, Hungary; Ravichandran Ramasamy, Dallas, Tex.

[73] Assignee: Board of Regents, The University of Texas System, Austin, Tex.

[*] Notice: The portion of the term of this patent subsequent to Jan. 27, 2004 has been disclaimed.

[21] Appl. No.: 615,619

[22] Filed: Nov. 19, 1990

Related U.S. Application Data

[63] Continuation-in-part of Ser. No. 357,193, May 25, 1989, abandoned, and Ser. No. 291,053, Dec. 28, 1988, Pat. No. 4,983,376, which is a continuation-in-part of Ser. No. 007,729, Jan. 27, 1987, abandoned, which is a continuation-in-part of Ser. No. 662,075, Oct. 18, 1984, Pat. No. 4,639,365.

[51] Int. Cl.$^5$ .................... A61K 49/00; C07D 255/02
[52] U.S. Cl. .................... 424/09; 540/465; 540/474
[58] Field of Search .................... 424/9; 540/465, 474; 534/15, 16

[56] References Cited

U.S. PATENT DOCUMENTS

| | | | |
|---|---|---|---|
| 3,930,867 | 1/1976 | Bigelow | 96/107 |
| 3,932,451 | 1/1976 | Bigelow | 430/78 |
| 3,987,128 | 10/1976 | Richman | 540/474 |
| 3,996,276 | 12/1976 | Atkins | 540/474 |
| 4,038,312 | 7/1977 | Atkins | 540/474 |
| 4,085,106 | 4/1978 | Atkins | 540/474 |
| 4,130,715 | 12/1978 | Atkins | 540/474 |

(List continued on next page.)

FOREIGN PATENT DOCUMENTS

| | | | |
|---|---|---|---|
| 0382582 | 8/1990 | European Pat. Off. | 540/465 |
| 0404605 | 12/1990 | European Pat. Off. | 540/465 |
| 3129906 | 7/1981 | Fed. Rep. of Germany | 424/9 |
| 3401052 | 1/1989 | Fed. Rep. of Germany | 424/9 |
| 2539996 | 1/1984 | France | 424/9 |
| 1081169 | 3/1984 | U.S.S.R. | 540/474 |
| 2137612A | 10/1084 | United Kingdom | 540/474 |
| 1529150 | 5/1977 | United Kingdom | 540/474 |

OTHER PUBLICATIONS

Cabbiness et al., "Macrocyclic Effect on the Stability of Copper (II) Tetramine Complexes", J. Am. Chem. Soc., 91(23):6540 (1969).

(List continued on next page.)

*Primary Examiner*—Mukund J. Shah
*Assistant Examiner*—Y. N. Gupta
*Attorney, Agent, or Firm*—Arnold, White & Durkee

[57] ABSTRACT

The present invention relates to a new polyazamacrocyclic compound or a salt thereof and its uses. The compound has the formula

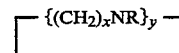

where
x is 2, 3 or a combination of p 2(s) and q 3(s) where p+q=y;
y is 3 or 4;
R is $(CH_2)_zP(=O)R^1R^2$;
$R^1$ is $R^3$ or $OR^3$ where $R^3$ is alkyl, cycloalkyl or aryl;
$R^2$ is H, alkyl or

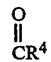

where $R^4$ is alkyl, cycloalkyl or aryl; and
z is 1 to 3.

In one important embodiment, this compound may be complexed with a metal to be a polyazamacrocyclic compound-metal complex having the formula

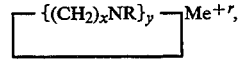

where
r is 2 or 3; and
Me is a metal ion.

5 Claims, 8 Drawing Sheets

U.S. PATENT DOCUMENTS

| | | | |
|---|---|---|---|
| 4,337,154 | 6/1982 | Fukuchi | 210/490 |
| 4,352,751 | 10/1982 | Wieder | 552/540 |
| 4,421,671 | 12/1983 | Cusano | 252/304 |
| 4,432,907 | 2/1984 | Wieder | 552/540 |
| 4,472,509 | 9/1986 | Gansow et al. | 436/819 |
| 4,639,365 | 1/1987 | Sherry | 540/465 |
| 4,647,447 | 3/1987 | Gries et al. | 424/9 |
| 4,731,239 | 3/1988 | Gordon | 424/9 |
| 4,735,796 | 4/1988 | Gordon | 424/9 |
| 4,957,939 | 9/1990 | Gries et al. | 424/9 |
| 4,963,344 | 10/1990 | Gries et al. | 424/9 |
| 4,983,376 | 1/1991 | Sherry | 540/465 |

OTHER PUBLICATIONS

Martin et al., "The Relationship between Metal–Donor Distance and Ring Size in Macrocyclic Complexes", J. Am. Chem. Soc., 96(12):4046 (1974).
Richman et al., "Nitrogen Analogs of Crown Ethers", J. Am. Chem. Soc., 96(7):2268–70 (1974).
Lettvin et al., J. Mag. Res., 28:459–61 (1977).
White et al., J. Amer. Chem. Soc., 101(17):4921 (1979).
Desreux, Inorganic Chemistry, 19:1319–24 (1980).
Sherry, "A Proposal on Basic Chemical Research", submitted to the Robert A. Walsh Foundation (1981).
Bryden et al., Chemical Abstracts, No. 97:206960z (1982).
Singh, Letter dated Apr. 13, 1983 to Sherry.
Desreux, letter dated Dec. 23, 1983 to Sherry.
Brasch et al., A. J. R., 142:625–30 (1984).
Chen et al., Fed. Euro. Biochem. Soc., 168(1):70 (1984).
Goldstein et al., Physiol. Chem. & Phys. & Med. NMR, 16:97–104 (1984).
Sherry, Letter dated Apr. 4, 1984 to Schmidt.
Weinmann et al., A. J. R., 142:619–24 (1984).
Wolf, Physiol. Chem. & Phys. & Med. NMR, 16:93–95 (1984).
Geraldes et al., Inorganic Chemistry, 24(23):3876 (1985).
Geraldes et al., Journal of Magnetic Resonance, 66:274–82 (1986).
Geraldes et al., Magnetic Resonance in Medicine, 3:242–50 (1986).
Sherry et al., Journal of Magnetic Resonance, 66:511–24 (1986).
Chavez et al., J. Org. Chem., 54(12):2990–92 (1989).
Sherry, J. Less Common Metals, 149:133–41 (1989).
Lazar et al. (1991) "N,N',N"-Tris(methoxymethyl)-1,4,7-triazacyclononane: a New Synthetic Tool for the Synthesis of Tris-N-substituted 1,4,7-Triazacyclononane Derivatives", J. Chem. Soc., Chem. Commun., Nr. 18:1252–1253, published in Great Britain.
Parker et al., "Preparation of tetraphosphinate-substituted tetraaza macrocycles for use as antitumor or imaging agents", Chem. Abstr. 114:122706c (1991) citing European Patent Application EP 382,582, Aug. 16, 1990.

POLYAZAMACROCYCLIC COMPOUNDS FOR COMPLEXATION OF METAL IONS

This is a continuation-in-part of U.S. Ser. No. 07/357,193 filed May 25, 1989 now abandoned and U.S. Ser. No. 07/291,053 filed Dec. 28, 1988 now U.S. Pat. No. 4,983,376 which are incorporated by reference herein. Application Ser. No. 07/291,053 was a continuation-in-part of application Ser. No. 007,729 filed on Jan. 27, 1987 now abandoned, which was a continuation-in-part of application Ser. No. 662,075, filed on Oct. 18, 1984, now issued as U.S. Pat. No. 4,639,365.

BACKGROUND OF THE INVENTION

The present invention relates to a series of new phosphorous containing macrocyclic chelates which bind certain biological ions with relative specificity. The $^{31}P$ resonance of these chelators shift to a new position in the NMR spectrum when a metal ion occupies the cavity of the chelate and the NMR chemical shift of the bound chelate differs for each metal ion. This property should be useful for monitoring the intracellular concentrations of certain biological cations including for example, $Mg^{2+}$, $Ca^{2+}$, and $Zn^{2+}$, by $^{31}P$ NMR. There are several fluorescent chelators commercially available for measuring intracellular cation concentrations and 1 or 2 fluorine containing chelators for NMR purposes. The fluorescent chelators will likely not be applicable for human studies and the $^{19}F$ chelators are not as likely to be applied clinically as the $^{31}P$ chelators of the present invention. Also, certain of the chelators when bound to $Gd^{3+}$ has properties which should make it a safe, effective contrast agent for magnetic resonance imaging.

A great number of biological systems require the diamagnetic cations, $Ca^{2+}$, $Mg^{2+}$, and $Zn^{2+}$ to regulate various reactions. The role of $Ca^{2+}$ as an intracellular messenger ion in many types of cells is well established [1]. $Mg^{2+}$ is a required cofactor for virtually all biological reactions involving ATP and may play an extensive role in the buffering of a greater variety of biological reactions [2]. $Zn^{2+}$ is bound rather tightly in the active sites of several enzymes and its role appears to involve polarization of chemical bonds to aid bond hydrolysis, oxidation-reduction, or group transfer reactions. However, free $Zn^{2+}$ may play a much wider role in some cells such as brain cells where it is known to be stored in neurons as storage granules and is mobilized during electrophysiologic activation [3].

An evaluation of the role of divalent cations in cell function has been limited by the availability of direct methods for measuring free cation concentration in cells and perfused organs. Presently available methods for measurement of divalent cations include indirect calculations based on equilibrium reactions [4], ion-selective micro-electrodes [5,6], and null point measurements using metallochromic dyes that are either microinjected into cells [7] or placed into the extracellular space with subsequent lysis of cells [8,9]. Virtually all of these methods are invasive in nature and require sample destruction prior to analysis. By contrast, NMR has made considerable advances as a non-invasive tool in measuring intracellular free divalent cation concentrations in perfused organs and intact cells.

Recently, fluorinated chelators have been effectively used to measure intracellular free $Ca^{2+}$ [10,11] and $Mg^{2+}$ [12,13] in cells and perfused organs by $^{19}F$ NMR. These chelators work reasonably well in isolated cell systems but suffer from unexpected line broadening when used in perfused organs [13,14]. Another disadvantage with these systems is the synthetic routes to these compounds limits the possible chelate structures and hence metal-ion selectivity that may be designed into the chelate. Aspects of the present invention include the synthesis and development of a series of triaza and tetraaza macrocylic phosphonate monoesters and alkyl phosphinates as $^{31}P$ NMR indicators to detect intracellular free cations in biological systems.

The present invention also relates to NMR imaging of living subjects, sometimes referred to as MRI (magnetic resonance imaging). More specifically, it relates to agents which can be used to enhance NMR contrast in such subjects.

Nuclear magnetic resonance (NMR) has been used for many years as a means of chemical analysis. NMR is a type of radio frequency spectroscopy which is based upon small energy differences between electrically charged atomic nuclei which are spinning parallel or antiparallel to an applied magnetic field. When radio frequency energy is applied to the sample, these spining atomic nuclei change spin states and in doing so, absorb some of the radio frequency energy. Nuclei in slightly different chemical environments within the same molecule change spin state at slightly different energies and this produces characteristic absorptions or resonances which help identify the molecular structure.

NMR has more recently been used in examinations of the human body. Other methods such as computerized axial tomography (CAT scanning) have been used in the past for this purpose, and still are. However, because NMR does not use ionizing radiation, it is believed to have some safety advantages over CAT. Thus, NMR is an advantageous method of producing cross-sectional images of the human body.

The quality of the images obtained from an NMR scan is based on two properties: the proton densities of the various tissues and differences in proton relaxation rates. The proton density of tissues cannot be readily altered. Proton relaxation rates can be adjusted by adding a paramagnetic relaxation agent, more commonly known as a "contrast agent." Contrast agents enhance the contrast in NMR images between magnetically similar but histologically dissimilar tissues.

Gadolinium has been tested as a contrast agent in the past because it has a large magnetic moment, which efficiently relaxes magnetic nuclei. Gadolinium's strong paramagnetic properties are the result of its seven unpaired electrons.

One drawback of gadolinium as a contrast agent is its toxicity to animals. One possible remedy for this problem is to incorporate gadolinium in a compound that would pass through the body and be excreted without releasing toxic gadolinium ions. Unfortunately, the rare earth elements, such as gadolinium, do not form stable covalent bonds with organic molecules, so such molecules can decompose in vivo and release the toxic ions.

There is a need for effective contrast agents which avoid the toxicity problems inherent in using gadolinium. Further, there is a need for new and better contrast agents, whether they include gadolinium or another paramagnetic metal.

SUMMARY OF THE INVENTION

The present invention relates to a new polyazamacrocyclic compound or a salt thereof and its uses. The compound has the formula where
x is 2, 3 or a combination of p 2(s) and q 3(s) where p+q=y;
y is 3 or 4;
R is $(CH_2)_zP(=O)OR^1R^2$
$R^1$ is $R^3$ or $OR^3$
$R^3$ is alkyl, cycloalkyl or aryl
$R^2$ is H, alkyl or $R^4$ is alkyl, cycloalkyl or aryl
($R^3$ and $R^4$ may or may not be equal in the same molecule)
z is 1 to 3

A preferable alkyl is $C_nH_{1+2n}$ where n is 1–20; a preferable cycloalkyl is $C_nH_{2m-1}$ when m is 1–20; and a preferable aryl is phenyl.

In one important embodiment, this compound may be complexed with a metal to be a polyazamacrocyclic compound-metal complex having the formula where
x is 2, 3 or a combination of p 2(s) and q 3(s) where p+q=y;
y is 3 or 4;
R is $(CH_2)_zP(=O)OR^1R^2$;
$R^1$ is $R^3$ or $OR^3$;
$R^3$ is alkyl, cycloalkyl or aryl;
$R^2$ is H, alkyl or z is 1 to 3;
r is 2 or 3; and
Me is a metal ion.

The y designation characterizes the compound as triazamacrocyclic or tetraazamacrocyclic. The x is preferably 2, although 3 is feasible under many circumstances. Combinations of p 2(s) and q 3(s) for x are of course readily produced but the total of p+q must be y for the number of units in the polyaza macrocycle.

In a preferred embodiment of either the compound or its metal complex y is 3, p is 1 and q is 2 or p is 2 and q is 1.

In another preferred embodiment of the compound or its metal complex, y is 4, p is 1 and q is 3, p is 2 and q is 2 or p is 3 and q is 1 and z is most preferably 1. n is preferably 2.

In a more preferred embodiment x is 2, y is 4, z is 1, and $R^1$ is $R^3$.

In another preferred embodiment X is 2, y is 3, z is 1, $R^1$ is $OR^2$ and n is 2.

The $Me^{+r}$ is preferably $Ca^{+2}$, $Mg^{+2}$, $Zn^{+2}$ or $Gd^{+3}$. Other characteristic divalent or trivalent metal ions, particularly paramagnetic lanthanides may also be so complexed.

The present invention comprises a method for assessing intracellular concentration of one or more divalent metal ions. The method comprising treating cells, under conditions facilitating intracellular localization of a polyazamacrocyclic compound or a salt thereof, the compound having the formula where
x is 2, 3 or a combination of p 2(s) and q 3(s) where p+q=y;
y is 3 or 4;
R is $(CH_2)_zP(=O)OR^1R^2$;
$R^1$ is $R^3$ or $OR^3$;
$R^3$ is alkyl, cycloalkyl or aryl
$R^2$ is H, alkyl or

$R^4$ is alkyl, cycloalkyl or aryl
z is 1 to 3 and measuring shifts in the $^{31}P$ NMR spectrum, said shifts being proportional to intracellular divalent metal concentration. In one embodiment cells are treated with the acid anhydride form of the compound of the present invention (i.e. where $R^2$ is which passes into the cells, is there hydrolyzed to the acid form (i.e. where $R^2$ is H) and complexes with intracellular metal ions. The metals currently most amenable to such measurement are calcium, magnesium or zinc, magnesium being preferred.

In one important application, the present invention involves a method for enhancing a magnetic resonance image of a subject. This method comprises administering to the subject a polyazamacrocyclic compound-metal complex having the formula where
x is 2, 3 or a combination of p 2(s) and q 3(s) where p+q=y;
y is 3 or 4;
R is $(CH_2)_zP(=O)OR^1R^2$;
$R^1$ is $R^3$ or $OR^3$;
$R^3$ is alkyl, cycloalkyl or aryl
$R^2$ is H, alkyl or $R^4$ is alkyl, cycloakyl or aryl
z is 1 to 3;
r is 2 or 3; and
Me is a paramagnetic metal (preferably gadolinium);
obtaining a magnetic resonance image of said subject.

BRIEF DESCRIPTION OF THE DRAWINGS

FIG. 4A and B shows $^{31}P$ NMR spectra of 5 mM NOTPME in the presence of (A) 2.05 mM $ZnCl_2$, and (B) 38.5 mM $CaCl_2$. Sample composition and spectral parameters are given in methods section.

DETAILED DESCRIPTION OF PREFERRED EMBODIMENTS

EXAMPLE 1

Triazamacrocyclic Compounds 1,4,7-Triazacyclononane-N,N',N"-tris(methylenephosphonate monoethylester) (NOTPME) has been synthesized, characterized and analyzed for use as a $^{31}P$ NMR indicator of intracellular $Mg^{2+}$ and $Zn^{2+}$ ions. The $^{31}P$ NMR spectrum of this chelate in the presence of metal ions shows characteristic resonances for the free chelate, Mg(NOTPME)$^-$, and Zn(NOTPME)$^-$ and Ca(NOTPME)$^-$. Stability constants for NOTPME complexes with $Ca^{2+}$ and $Mg^{2+}$ have been determined by potentiometry and NMR and its complex with $Zn^{2+}$ by potentiometry. This chelate has a 10 fold higher affinity for $Mg^{2+}$ than for $Ca^{2+}$ at physiological pH values. Its affinity for $Zn^{2+}$ is so high that accurate binding constants could not be determined by NMR. In the presence of $Mg^{2+}$, NOTPME is readily loaded into red blood cells. $^{31}P$ chemical shifts of the free chelate and its metal complexes are far downfield from the typical phosphorous containing metabolites observed in biological systems, thus making it possible to monitor intracellular cation concentration and cell energetics simultaneously.

MATERIALS AND METHODS

Materials 1,4,7-triazacyclononane, paraformaldehyde, diethylphosphite, and activated carbon Darco G-60 were purchased from Aldrich Chemical Company. $MgSO_4$ was from Mallickrodt, sodium hydroxide, and benzene from J. T. Baker, and diethylether from Fisher Scientific. All chemicals were of highest purity and were used without further purification. Solutions of $ZnCl_2$, $CdCl_2$, $MgCl_2$ and $CaCl_2$ were standardized complexometrically.

Figure 1:
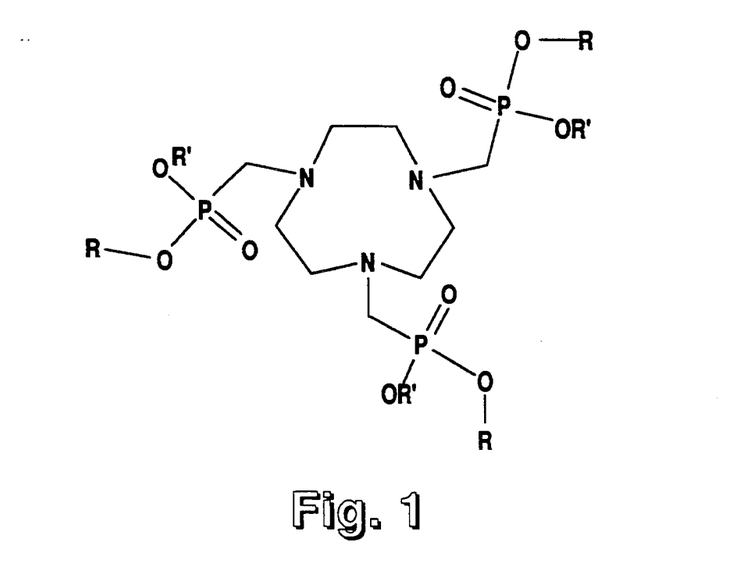
FIG. 1 schematically illustrates the structure of NOTPME (where R is $CH_2CH_3$ and $R^1$ is H).

Synthesis of NOTPME 1,4,7-Triazacyclononane (1.91 g, 14.71 mmol) and diethylphosphite (7.018 g, 16.94 mmol, 15% excess) were dissolved in 125 ml of benzene and heated to reflux. Anhydrous paraformaldehyde (1.727 g, 30% excess) was added in small portions to the above refluxing mixture while the benzene-water azeotropic mixture was removed by distillation. After the addition of paraformaldehyde was complete, the entire solution was boiled for 30 minutes and then evaporated to obtain a yellow viscous oil. The oil was dissolved in 150 ml anhydrous diethylether and dried with anhydrous $MgSO_4$ overnight. $MgSO_4$, along with a white precipitate which formed, were filtered off and discarded. The filtrate was decolorized with activated carbon and filtered. The filtrate was evaporated in vacuum to obtain a viscous oil of 1,4,7-triazacyclononane-N,N',N"-tris(-methylenephosphonate diethylester) (NOTPDE). Pure NOTPDE was obtained in 96% yield (9.21 g, 14.17 mmol) and was used for the synthesis of NOTPME (structure shown in FIG. 1) without further purification. $^1H$ NMR data of NOTPDE in $CDCl_3$ (TMS at zero) are as follows: $\delta$ (ppm): 1.33 (t, 18H, —$CH_3$), 2.97 (s, 12H, N—$CH_2$), 3.00 (d, 6H, P—$CH_2$), 4.13 (p, 12H, O—$CH_2$).

9.20 g of NOTPDE (14.15 mmol) was mixed with 2.50 g of NaOH in 9 ml $H_2O$) and after 2 hours the entire reaction mixture was boiled until a clear solution was obtained (approximately 5 minutes). The solution was cooled to room temperature and was allowed to stand overnight. The crystals formed were filtered off from the viscous mother liquor using a pressure filter funnel with a coarse porosity grade filter disc. The crystals were washed once with cold absolute ethanol, three times with absolute ethanol-diethylether (1:1) mixture and finally with diethyl ether. The crystals of $Na_3NOTPME$ were dried in dry nitrogen stream at 25° C. for 2 hours. Traces of $H_2O$ and ethanol were removed upon vacuum drying (10 mm Hg) NOTPME for 5 hours at 50° C. Pure NOTPME thus obtained were white crystals, very hygroscopic, readily soluble in $H_2O$, and fairly soluble in chloroform. The yield of pure NOTPME was 40.8% (3.24 g, 5.77 mmol).

$^1H$ NMR ($D_2O$, HDO peak set as reference at 4.90 ppm), $\delta$(ppm): 1.23 (t, 9H, —$CH_3$), 2.54 (s, broad, 6H, P—$CH_2$), 2.79 (s, broad, 12 H, N—$CH_2$), 3.91 (p, 6H, O—$CH_2$).

NMR Measurements $^1H$ NMR data was obtained on JEOL FX—200 NMR spectrometer using a 10 mm probe operating at room temperature. Studies on solutions of NOTPME and its complexes were performed on a General Electric GN—500 NMR spectrometer. A 10 mm broad band probe was tuned to 202.4 MHz for $^{31}P$ detection. Shifts for NOTPME and its complexes were measured using 85% $H_3PO_4$ as an external standard. Probe temperatures were accurate to ±0.5° C.

Samples of NOTPME used for $K_D$ determinations by NMR consisted of 115 mMKCl, 20 mM NaCl and 10 mM HEPES buffered with Tris base at pH 7.4. Varying concentrations (typically 0.5 to 10 mM) of $Mg^{2+}$, $Ca^{2+}$ or $Zn^{2+}$ were added to the sample and the resulting $^{31}P$ NMR spectrum obtained. Resonance areas were determined by integration of peaks using the GE software.

Potentiometric Measurements

Potentiometric titrations were conducted at 25° C. using a Corning Ion Analyzer (model 250) and a Metrohm Dorsimat automatic burette (Brinkman Instruments). The hydrogen ion concentration was obtained from the measured pH values by the method suggested by Irving et al. [15]. $Na_3NOTPME$ was dissolved in 0.1M tetramethylammonium chloride, the pH adjusted to low pH value with HCl and titrated with 0.098M KOH. KOH was standardized by potentiometric titration against potassium hydrogen phthalate and stored under $N_2$ atmosphere. The hydrogen ion activity coefficient and $K_w$ were determined separately in these same salt solutions. Stability constants of $Zn(NOTPME)^-$, $Mg(NOTPME)^-$, and $Ca(NOTPME)^-$ were determined by potentiometric titration of solutions containing 1:1 ratio of metal and ligand. In all of the titrations, samples were covered by a layer of cyclohexane to exclude $CO_2$.

Protonation constants ($K_{HiL}$) and stability constants ($K_{ML}$, and $K_{MHL}$) are defined by the following equations:

$$K_{HiL} = [H_iL]/\{[H_{i-1}L]\{H^+\}\} \quad (1)$$

$$K_{ML} = [ML]/\{[M][L]\} \quad (2)$$

$$K_{MHL} = [MHL]/\{[ML][H^+]\} \quad (3)$$

Protonation and stability constants were obtained from the potentiometric data using a simplex non-linear algorithm [16] run on an IBM PC.

Red Blood Cell Loading of NOTPME

Fresh whole blood was obtained placed in heparinized tubes and centrifuged at 3000 g for 6 min. to remove the buffy coat. RBCs were then washed three times in 5 mM phosphate buffered saline at pH 7.4. RBCs at 50% hematocrit were suspended in the loading medium containing 120 mM NaCl, 5 mM $MgCl_2$, 10 mM HEPES pH 7.4, 10 mM glucose, and 10 mM NOTPME and incubated at 37° C. for 12 hours. No lysis of RBCs were observed during the loading procedure. The RBCs were centrifuged and the supernatant discarded. The RBCs were washed twice with phosphate buffered saline at pH 7.4 before suspension in an isotonic medium.

RESULTS

Protonation Studies

Figure 2:
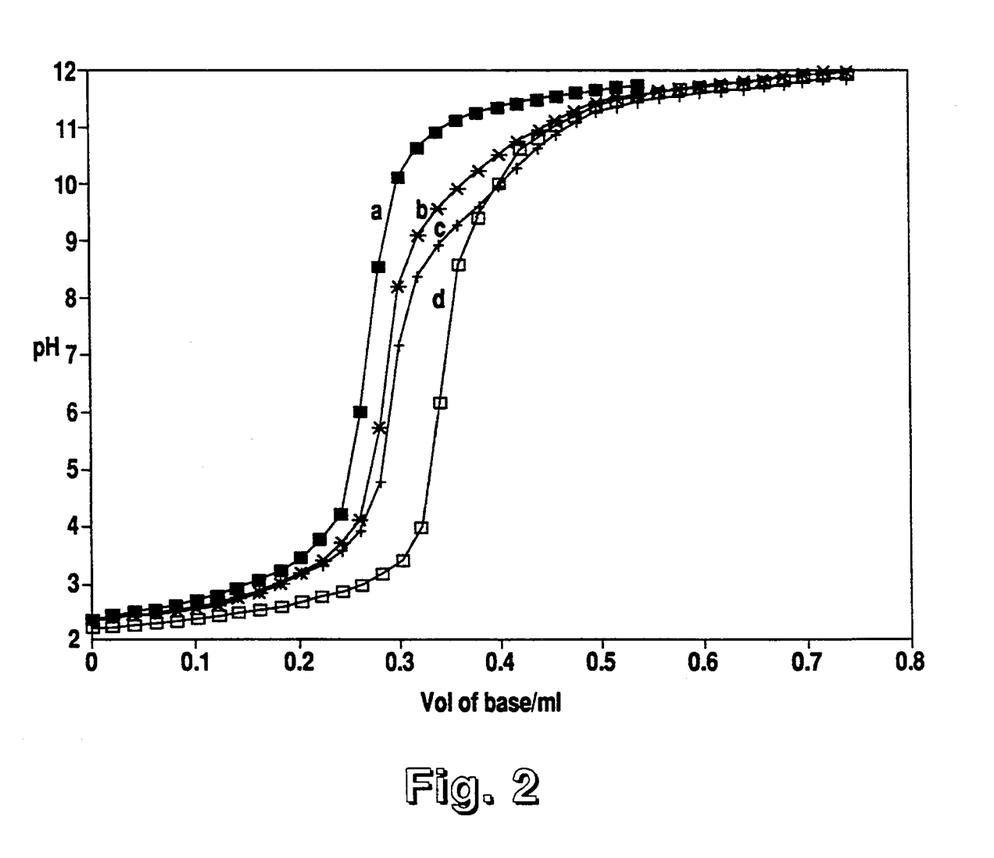
FIG. 2 describes potentiometric titration curves of 2 mM NOTPME (a) and those obtained in the presence of equivalent amounts of $Ca^{2+}$ (b), $Mg^{2+}$ (c), and $Zn^{2+}$ (d).

A representative potentiometric titration curve for NOTPME in 0.1M tetramethylammonium chloride and 25° C. is illustrated in FIG. 2. Three protonation constants ($pK_1 = 11.8$, $pK_2 = 3.65$, and $pK_3 = 1.4$) were obtained from these data. The $^{31}P$ NMR spectrum of NOTPME was also measured as a function of pH (data not shown) and the protonation constants obtained from these data were in general agreement with those obtained by potentiometry. The phosphorous shifts are very sensitive to protonation of the nitrogens in the polyaza ring, similar to that observed for the parent phosphonate NOTP [17]. The first two protonations (log K = 11.8, 3.65) result in $^{31}P$ shifts to low frequency which is consistent with protonation at two ring nitrogens [17]. This indicates that the first nitrogen protonations in NOTP versus NOTPME are quite similar (log $K_1 = 12.1$ versus 11.8, respectively) while the second nitrogen protonations are dramatically different (log $K_2 = 9.4$ versus 3.65). These differences in $pK_2$ may reflect differences in the ability of the phosphonate versus the phosphonate monoester side chains to form internal hydrogen bonds with the protonated nitrogens. This would be consistent with the greater basicity of the phosphonate oxygens in NOTP (protonation constants between 6.0 and 7.5) over the phosphonate ester oxygens in NOTPME (protonations below 1.4). $^{31}P$ NMR spectra of NOTPME exhibited a single resonance over the entire pH range, indicating rapid exchange between all protonated species.

Complexation Studies

FIG. 2 also shows potentiometric titration data for NOTPME in the presence of one equivalent of $Mg^{2+}$, $Ca^{2+}$, or $Zn^{2+}$. The stability constants for $Mg(NOTPME)^-$, $Ca(NOTPME)^-$, and $Zn(NOTPME)^-$ derived from these data are summarized in Table I.

TABLE I

| | Stability constants of the NOTPME complexes with $Ca^{2+}$, $Mg^{2+}$, and $Zn^{2+}$. | | |
|---|---|---|---|
| Metal ion | $K_D$ (at 25° X.) | $K_D$ (at 37° C.) | log $K_{ML}$ |
| $Ca^{2+}$ | 50 mM | 47.62 mM | 5.1 |
| $Mg^{2+}$ | 5.77 mM | 4.66 mM | 6.3 |
| $Zn^{2+}$ | $(10^{-11} M)^a$ | — | 15.4 |

$K_D$ values were obtained from NMR data while log K values were determined by potentiometry at 25° C. $^aK_D$ estimated from the thermodynamic value (log $K_{ML} = 15.4$) by considering the ligand pK values and the proton concentration at pH 7.4.

$Zn^{2+}$ forms a considerably more stable complex with NOTPME than either $Mg^{2+}$ or $Ca^{2+}$. This largely reflects the propensity of $Zn^{2+}$ to form stronger $M^{2+}$-N bonds than more ionic species, $Mg^{2+}$ and $Ca^{2+}$. Both $Mg(NOTPME)^-$ and $Ca(NOTPME)^-$ are less stable than their respective NOTP complexes [18], which again reflects the more acidic nature of phosphonate ester side-chain ligands. However, NOTPME, like NOTP forms more stable complexes with the smaller $Mg^{2+}$ ion than with $Ca^{2+}$. This reflects the size selectivity of the triazacyclononane macrocycle in both cases.

Figure 3:
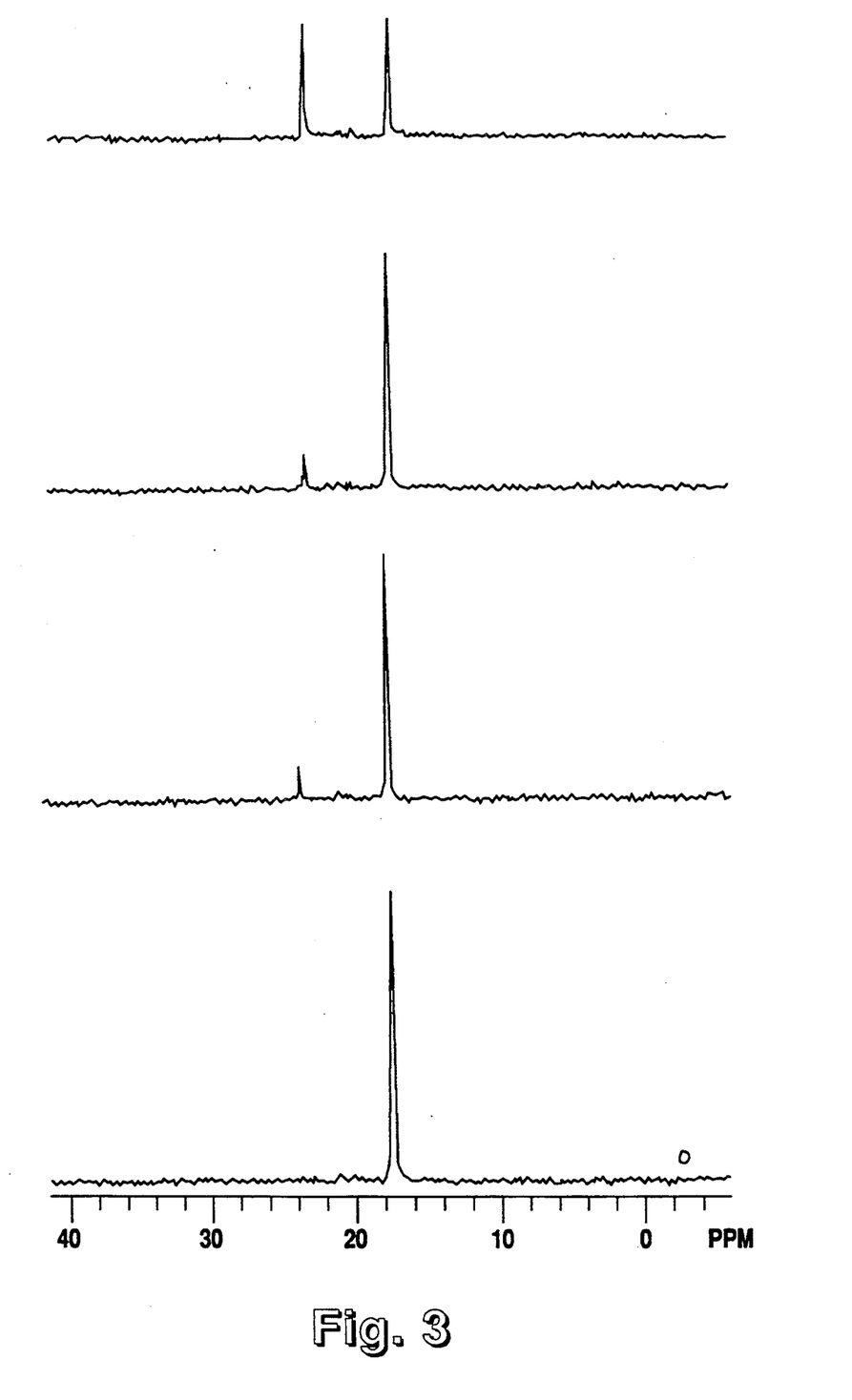
FIG. 3 shows $^{31}P$ NMR spectra of 5 mM NOTPME as a function of added (total) magnesium. $Mg^{2+}$ concentrations from bottom to top are 0, 0.5, 1.5, 3 mM respectively. Sample constituents and spectral parameters are described in methods section.
Figures 4A, 4B:
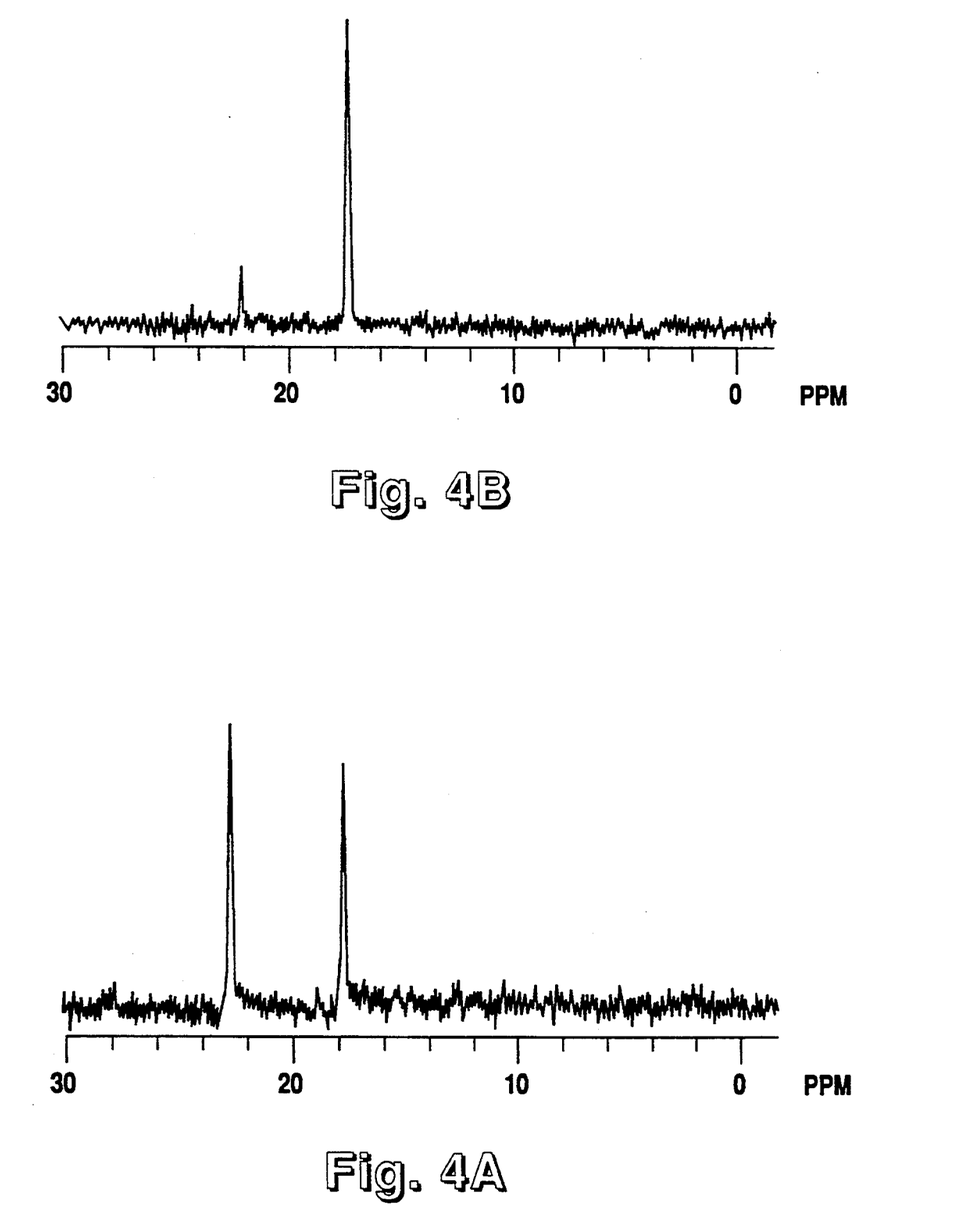

FIG. 3 displays the $^{31}P$ NMR spectrum of a solution containing 5 mM NOTPME as a function of added $Mg^{2+}$. The spectra show that $Mg^{2+}$ bound NOTPME is in slow exchange with "free" NOTPME. FIG. 4 shows $^{31}P$ NMR spectra of 5 mM NOTPME in the presence of 2.05 mM $Zn^{2+}$ and 38.5 mM $Ca^{2+}$. As expected based upon the potentiometrically determined stability constants, there is more $Zn(NOTPME)^-$ present in this solution than in an equivalent solution containing $Mg^{2+}$. Interestingly, the chemical shifts of $Mg^{2+}$ and $Zn^{2+}$ bound NOTPME are quite different and, indeed, it is possible to obtain characteristic resonances for Zn(NOTPME) and Mg(NOTPME) in a mixture containing both metal ions. $Ca^{2+}$, as expected, binds much more weakly and a resonance characteristic of Ca(NOTPME)$^-$ only becomes visible after 32 mM $Ca^{2+}$ has been added. The chemical shift of Ca(NOTPME)$^-$ (22.1 ppm) was also different form those of Mg(NOTPME)$^-$ (23.5 ppm) and Zn(NOTPME)$^-$ (23.1 ppm). This probably reflects the larger size of $Ca^{2+}$ versus $Mg^{2+}$ or $Zn^{2+}$ and its inability to fit into the cyclononane cavity.

The area of resonances corresponding to free and metal bound NOTPME were obtained by integration and their concentrations estimated. The $K_D$ values obtained at 25° C. by NMR for $Mg^{2+}$ and $Ca^{2+}$ complexes are 5.77 mM and 50 mM, respectively. In comparison, the fluorinated chelator, MF-APTRA, reported by others [12] has a $K_D$ of 1 mM for $Mg^{2+}$ and 12 $\mu$M for $Ca^{2+}$.

Table I also shows the $K_D$ for Mg(NOTPME)$^-$, and Ca(NOTPME)$^-$ obtained by NMR at 37° C. Clearly, the magnitude of differences in stabilities between Mg(NOTPME)$^-$, and Ca(NOTPME)$^-$ at 37° C. remain the same. This reconfirms the higher affinity of NOTPME for $Mg^{2+}$ over $Ca^{2+}$ at physiological temperature. It was not possible to obtain $K_D$ values for Zn(NOTPME)$^-$ from the NMR data because the titrated $Zn^{2+}$ was completely bound to NOTPME under virtually all measurable conditions.

Figure 5:
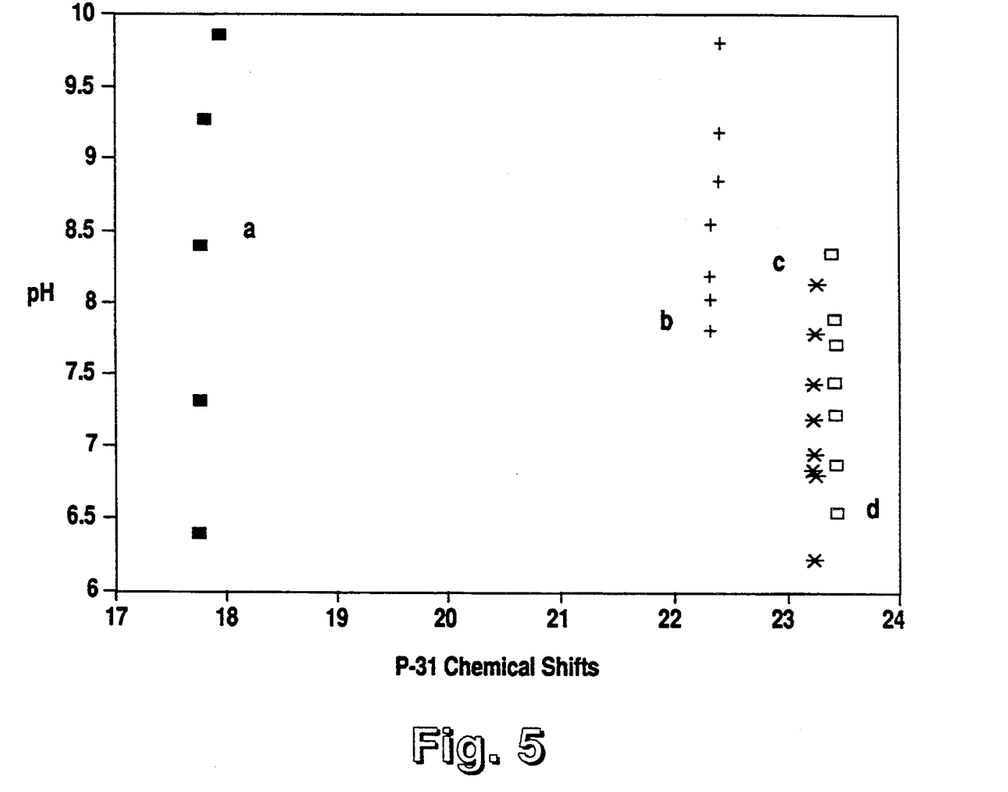
FIG. 5 describes pH dependence of the $^{31}P$ NMR chemical shifts of 5 mM NOTPME (a), Ca(NOTPME)$^-$(b), Zn(NOTPME)$^-$(c), and Mg(NOTPME)$^-$(d).

FIG. 5 shows the $^{31}P$ NMR chemical shifts of the NOTPME complexes of $Ca^{2+}$, $Mg^{2+}$, and $Zn^{2+}$ as a function of pH between 6 and 10. In solutions containing 1:1 metal ion and ligand, the resonance characteristic of Zn(NOTPME)$^-$ is visible over this entire pH range, that characteristic of Mg(NOTPME)$^-$ is detectable only above pH 6.4, while that characteristic of Ca(NOTPME)$^-$ is only visible above pH 7.8. These differences clearly demonstrate the greater selectivity of NOTPME for $Mg^{2+}$ over $Ca^{2+}$ at physiological pH (ca. 7.4). As shown, chemical shifts of the metal bound species are all virtually independent of pH over this range.

Figure 6A:
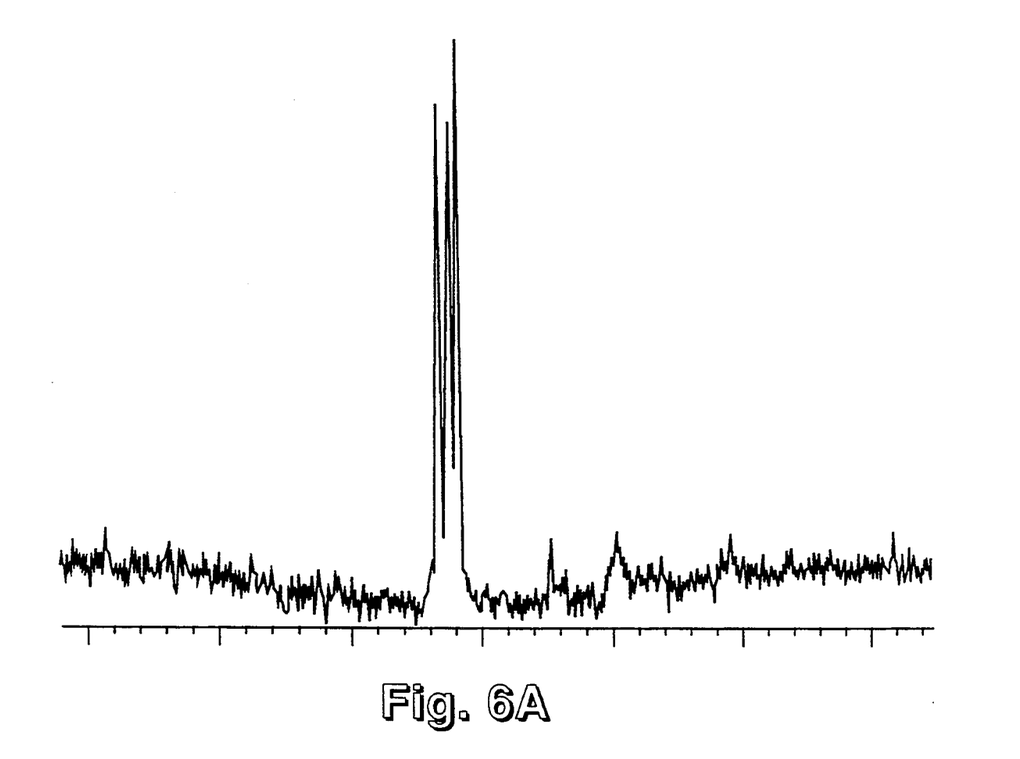
FIG. 6A and B shows $^{31}P$ NMR spectra of (a) normal RBCs and (b) NOTPME loaded RBCs.
Figure 6B:
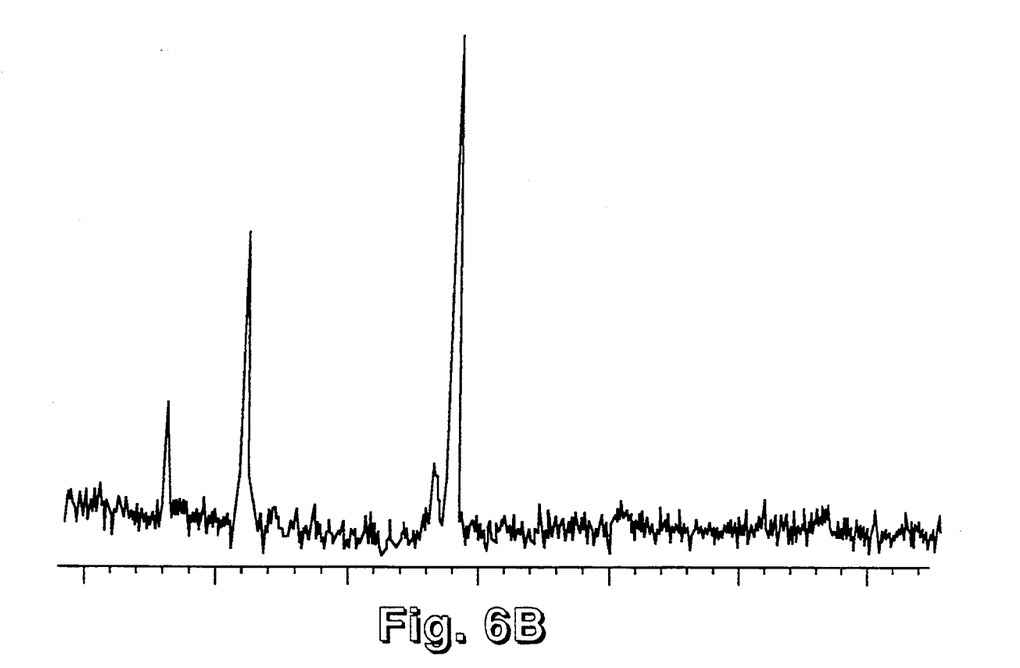

Determination of Intracellular Free $Mg^{2+}$ Concentration in Human Erythrocytes FIG. 6 illustrates one application of NOTPME to detect intracellular free $Mg^{2+}$ in RBCs. NOTPME loaded RBCs (FIG. 6b) were prepared by incubating RBCs at 37° C. in a loading medium containing NOTPME in the presence of 5 mM $MgCl_2$ for 12 hours. NOTPME loading into RBCs was not observed in the absence of $MgCl_2$ in the loading medium. Control RBCs are shown in FIG. 6a.

As in the in vitro studies, two resonances were observed corresponding to free and $Mg^{2+}$ bound NOTPME in RBCs. The intracellular free $Mg^{2+}$ concentration in RBCs was estimated using the following equation:

$$[Mg^{2+}] = K_D[MgNOTPME]/[NOTPME]$$

An intracellular free $Mg^{2+}$ concentration of 1.71 mM was obtained in this particular example. Since intracellular free $Mg^{2+}$ levels in RBCs normally range between 0.2–0.3 mM [12,19,20], the high concentration of intracellular free $Mg^{2+}$ observed in this experiment must have resulted from transport of $Mg^{2+}$ as a complex with NOTPME. Upon addition of the divalent cation ionophore A23187 to the suspension medium, an increase in intracellular free $Mg^{2+}$ concentration (to 1.90 mM) was observed (data not shown). These results show that NOTPME can easily detect small changes in free $Mg^{2+}$ levels in intact cells.

DISCUSSION

The complex forming characteristics of NOTPME are strongly influenced by the very high value of the first protonation constant as well as by the conformational and size requirements of the triaza ring. The fact that $Zn^{2+}$, $Ca^{2+}$, and $Mg^{2+}$ complexes of NOTPME could be studied by usual potentiometric method indicates that the complexes are formed relatively quickly in solution. As seen in Table I, $Zn^{2+}$ forms a more stable complex with NOTPME than does either $Mg^{2+}$ or $Ca^{2+}$. This same trend was observed for the triazacyclononane triacetate chelate, NOTA, with these same ions; reported log K values for Zn(NOTA)$^-$, Mg(NOTA)$^-$, and Ca(NOTA)$^-$ are 18.3, 9.69, and 8.92, respectively [21]. Thus, the carboxylate chelate forms more stable complexes with all three metal ions perhaps due to the greater basicity of the carboxylate oxygen ligands over the phosphonate oxygen ligands. The parent phosphonate, NOTP, shows the same trend in its metal complexing ability with $Zn^{2+}$, $Mg^{2+}$, and $Ca^{2+}$ but in this case the stability constants of the resulting complexes are all several orders of magnitude higher than the corresponding values with NOTPME or NOTA. The reported log K values for Zn(NOTP)$^{4-}$, Mg(NOTP)$^{4-}$, and Ca(NOTP)$^{4-}$ are 24.9, 11.0, 6.4 respectively [18]. Since the nitrogens and the phosphonate oxygens in NOTP are considerably more basic than those in NOTPME, the resulting stability constants with these metal ions are all larger. The trend $Zn^{2+} >> Mg^{2+} > Ca^{2+}$, however, is preserved.

NOTPME has several advantages over the fluorinated chelators such as BAPTA and APTRA for measurement of intracellular $Mg^{2+}$ in biological systems. These include (a) ease of synthesis, (b) higher affinity for $Mg^{2+}$ than for $Ca^{2+}$, (c) no significant exchange contribution to the bound and free ligand resonances, and (d) the three magnetically equivalent $^{31}P$ nuclei in this chelate provides an attractive NMR nucleus for biological tissue since the cell energetics may be measured simultaneously. The significant selectivity for $Mg^{2+}$ over $Ca^{2+}$ exhibited by NOTPME at physiological pH is of great advantage for monitoring $Mg^{2+}$ in biological systems without concern about interference from $Ca^{2+}$. It is important to emphasize that the resonances of NOTPME and its magnesium complex do not overlap with the phosphorous containing metabolites in tissue. Thus NOTPME provides versatile approach of measuring changes in intracellular free magnesium as well as changes in metabolites during various physiological events by $^{31}P$ NMR. Although it is fortuitous that the $K_D$ Mg(NOTPME)$^-$ at physiological pH is in the range required for measurement of intracellular $Mg^{2+}$ in many biological systems, it may prove possible to fine tune the affinity of NOTPME for $Mg^{2+}$ by changing the alkyl substituents on the phosphonate oxygens or by adding an alkyl chain to the carbon which links the phosphonate groups to the triaza ring.

EXAMPLE 2

Tetraazamacrocyclic compounds

DOTEP Synthesis

Figure 7:
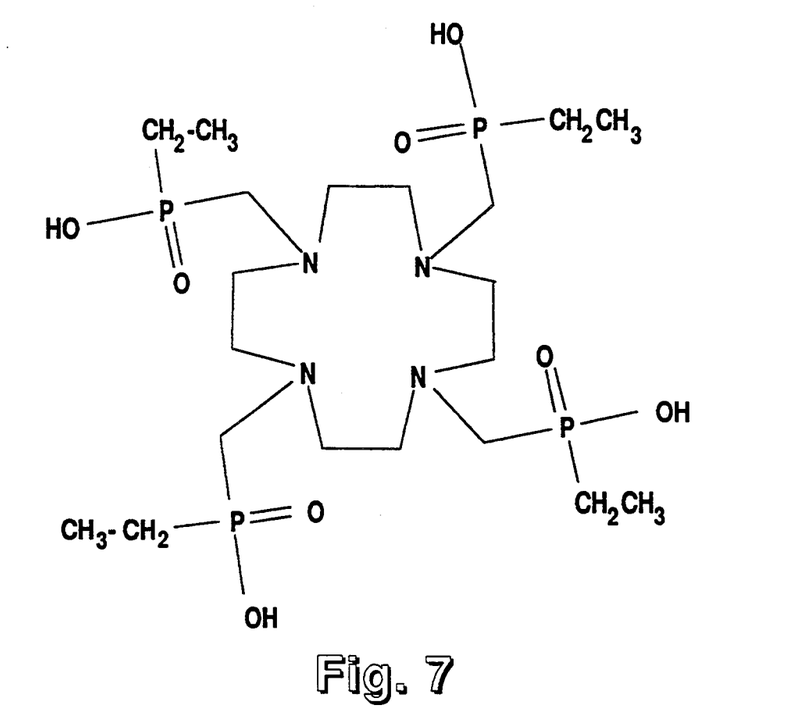
FIG. 7 schematically illustrates the structure of DOTEP.
Figure 8:
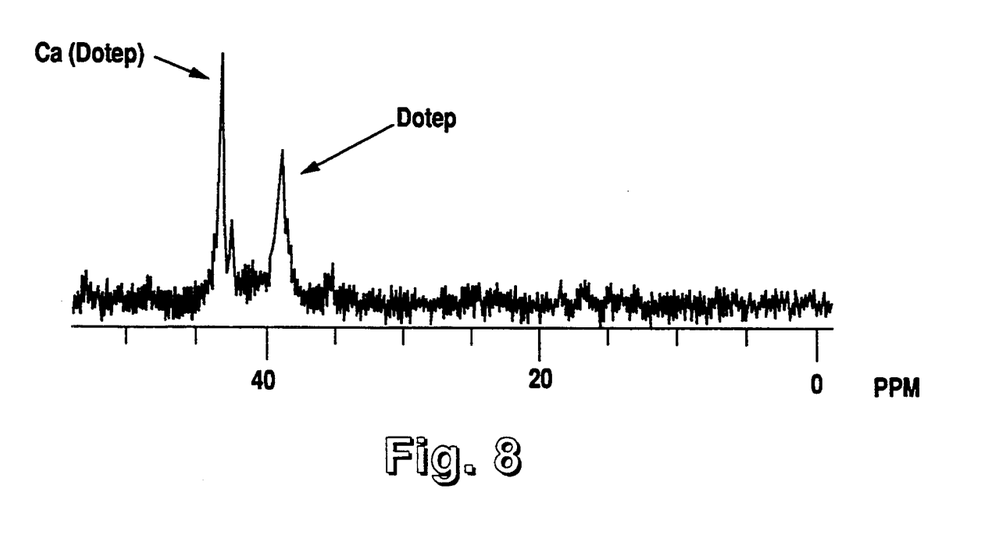
FIG. 8 shows the $^{31}P$ NMR spectrum of DOTEP and a DOTEP-calcium complex.

DOTEP, shown in FIG. 7, was prepared as follows. 2 ml of dichloroethylphosphine was slowly mixed with ice to form the corresponding ethylphosphinic acid. After warming to room temperature, 390 mg of 1,4,7,10-tetraazacyclododecane tetrahydrochloride (cyclen.4HCl) (Parrish Chem. Co., Ogden, Utah) was added and the mixture heated to boiling under a nitrogen atmosphere. A solution containing 157 mg of paraformaldehyde dissolved in 10 ml of 6M HCl was added at a rate of 0.5 ml/hr, while the mixture continued to reflux. The final mixture was refluxed an additional 4 hours then cooled to room temperature. This solution was concentrated under vacuum to a viscous oil, redissolved into 6 ml of water and loaded onto a DOWEX 50W=4 (hydrogen form) cation exchange column (7.5 ml bed volume). The column was washed to neutrality with water and the product eluted with 60 ml of 0.66M HCl. The fractions containing DOTEP were combined, evaporated, redissolved in absolute ethanol and evaporated to a white solid. This solid was dispersed into anhydrous ether, filtered off, pre-dried under nitrogen and dried under vacuum at 60°–70° C. to yield a white, very hygroscopic solid (360 mg, 44% yield). This solid was stored in sealed ampoules. Elemental analysis and potentiometry shows the solid to be DOTEP.2HCl

DOTEP APPLICATIONS

A. Ca(DOTEP)− as a $^{31}$P NMR indicator of [Ca$^{2+}$]$_{free}$

Figure 9:
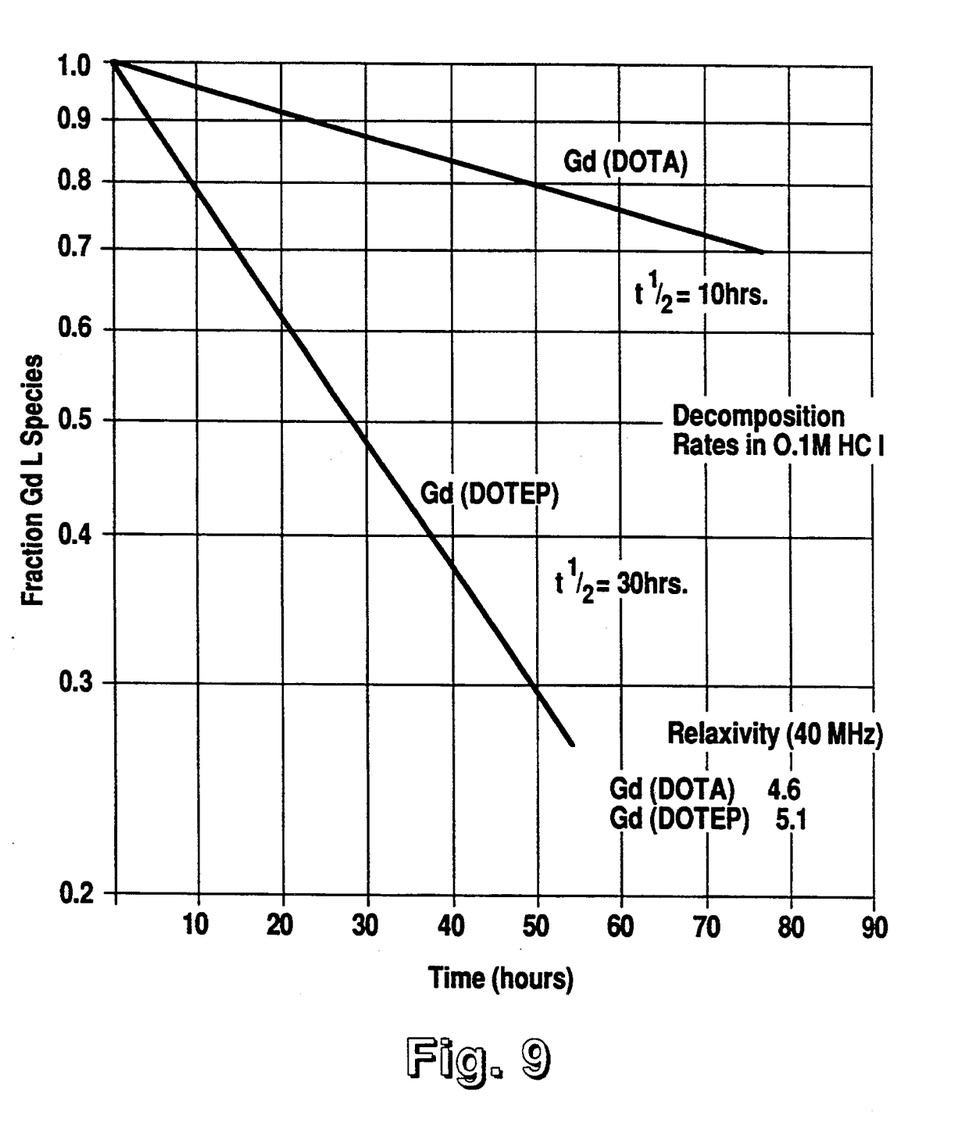
FIG. 9 describes the decomposition rate of gadolinium DOTA and gadolinium-DOTEP complexes in 0.1N HCl.

The $^{31}$P spectrum shown in FIG. 9 was obtained on a solution containing approximately 1 mM Ca$^{2+}$ and 3 mM DOTEP in an aqueous solution at physiological pH. Clearly, the $^{31}$P resonances of the free and bound forms of DOTEP have distinct chemical shifts and neither overlaps with the $^{31}$P resonances of metabolites normally observed in tissue. This indicates that when DOTEP is loaded into cells by making an appropriate hydrolysable ester, the DOTEP trapped in cells would give a direct measure of [Ca$^{2+}$]$_{free}$ using the simple relationship, $$[Ca^{2+}]_{free} = K_D \cdot \frac{[Ca(DOTEP)]}{[DOTEP]_{free}}$$

where $K_D = 11\ \mu M$ at H 7.4

The value of $K_D$ at pH 7.4 reported above was determined by $^{31}$P NMR (measuring the free and bound integrals as a function of pH in solutions containing known amounts of [Ca$^{2+}$]$_{total}$ and [DOTEP]$_{total}$) and by pH potentiometry. This value of $K_D$ indicates that DOTEP will be useful for measuring [Ca$^{2+}$]$_{free}$ over the approximate range, 1–50 μM.

B. Gd(DOTEP)− as a MRI contrast agent.

Figure 10:
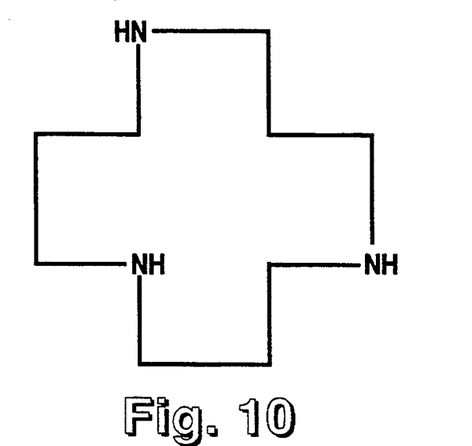
FIG. 10 schematically shows the compound 1,5,9-triazacyclododecane.

DOTEP also forms stable complexes with Gd$^{3+}$ (log K approximately equal to 16). The resulting complex has a favorable water proton relaxivity (R=5.1 s$^{-1}$mM$^{-1}$) and the complex has many of the same kinetic advantages as Gd(DOTA)−, as shown by the data of FIG. 10. In this experiment, Gd(DOTEP)− and Gd(DOTA)− were dissolved in 0.1M HCl and their decomposition to free Gd$^{3+}$ and free ligand were followed by water relaxation measurements. As shown, the half-lives for decomposition of the two complexes in strong acid were approximately 110 hrs. for Gd(DOTA)− versus 30 hrs. for Gd(DOTEP)−. This indicates that the decomposition rates for both complexes at pH 7.4 will be several orders of magnitude longer than this (or about 10$^6$ hrs.) and therefore should be quite safe for use in humans.

EXAMPLE

Polyazamacrocyclic N-alkyl phosphonate or phosphine acid anhydrides

Synthesis of NOTPME-AC

[NOTPME-AC=1,4,7-triazacyclononane-N,N',N''-tris(methylenephosphonate monoethylester acetic acid anhydride)]

NOTPME trisodium salt (178.63 mg, 0.318 mmol) was dissolved in 4.0 ml anhydrous chloroform (freshly distilled from over P$_4$O$_{10}$) and 120 microliter acetyl chloride was added. The solution was stirred at room temperature for 24 hours in a tightly closed vessel. The solution was then evaporated under dry nitrogen atmosphere to a yellowish, very viscous oil. To the oil anhydrous ether was added and NOTPME-AC (precipitated as a sodium chloride adduct) was filtered off and dried at 35°–40° C. under dry nitrogen. NOTPME-AC (234.24 mg, 92.3% calculated on the basis of NOTPME-AC.3NaCl formula weight) is an extremely hygroscopic, water sensitive powder. It is readily soluble in water, chloroform and DMSO.

$^1$H NMR (CDCl$_3$/TMS): 1.31(t,9H,—CH$_3$), 2.24 & 2.21 (two sg(s), 9H, C(O)—CH$_3$), 3.29 (sg, v.br.,18H, N—CH$_2$—C and N—CH$_2$—P), 4.12 & 4.30 (two m(s), 6H, O—CH$_2$).

Synthesis of NOTPME-B

[NOTPME-B=1,4,7-triazacyclononane-N,N',N''-tris(-methylenephosphonate monoethylester benzoic acid anhydride]

NOTPME trisodium salt (164.82 mg, 0.294 mmol) and benzoyl chloride (105 microliter, 0.883 mmol) were reacted in 4.0 ml anhydrous chloroform at room temperature for 24 hours. The reaction mixture was worked up with identical method than was used in the synthesis of NOTPME-AC. The product NOTPME-B was get as a sodium chloride adduct (204.32 mg, 70.7% calculated on the basis of NOTPME-B.3NaCl formula weight). NOTPME-B is a very hygroscopic, water sensitive powder. It is soluble in water and chloroform and DMSO.

$^1$H NMR (CDCl$_3$/TMS): 1.29 (t,—CH$_3$), 3.32 (m, V.br., N—CH$_2$—C and N—CH$_2$—P), 4.10 & 4.35 (two m(s), O—CH$_2$), 7.49 (m, At—H), 8.02 (d,Ar—H).

It is understood to those of skill in the art that a variety of aryl halides may be used to prepare analogous phosphonate or phosphine acid anhydrides with only a minimum of efforts to define optimal synthetic procedures. Additionally, it is clear that facile leaving groups such as carbonyl-containing alkyls may be preferred for greater stability in an aqueous medium and yet still pass into cells for partial decomposition and use in NMR metal analyses.

Red Blood Cell Loading of NOTPME Derivatives

NOTPME derivatives used are the benzoyl and acetyl derivatives. Fresh whole blood was obtained in heparinized tubes and centrifuged at 3000 g for 3 minutes to remove the buffy coat. Packed red blood cells are then washed three times in 5 mM phosphate buffered saline at pH 7.4. Red blood cells at 50% hematocrit were suspended in the NOTPME derivative containing loading medium. The loading medium contained 130 mM NaCl, 5 mM NOTPME derivative (benzoyl or acetyl derivative), 1 mM adenine, 10 mM glucose, and 10 mM HEPES at pH 7.4. Red cells in the above loading medium were incubated at 25° C. for 1 hour. No lysis of red blood cells were observed during the loading procedure. After loading with NOTPME derivatives for one hour, the red cell suspension was centrifuged and the supernatant discarded. The red cells are washed twice with 5 mM phosphate buffered saline at pH 7.4 before suspension in an isotonic saline for NMR measurements. The $^{31}$P NMR measurements indicated that these NOTPME derivatives get loaded inside red cells and get hydrolysed to NOTPME. After NMR measurements the sample was centrifuged and the supernatant analyzed for any leakage of NOTPME. No leak of NOTPME was observed during the time course of NMR measurements. Thus, it is clear that these NOTPME derivatives enter the red cells, get hydrolyzed to NOTPME and remain inside red cells.

EXAMPLE 4

Figure 11:
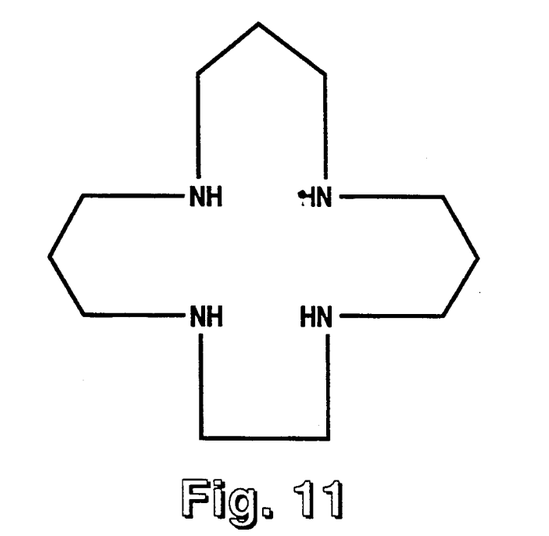
FIG. 11 schematically shows the compound 1,4,8,12-tetracyclopentadecane.
Figure 12:
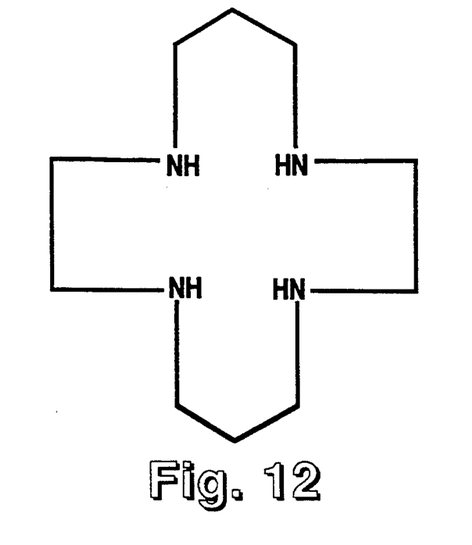
FIG. 12 schematically shows the compound 1,4,8,11-tetraazacyclotetradecane.

Prophetic Synthesis of Generic Polyazamacrocyclic N-Alkylphosphonates, Polyazamacrocyclic N-Alkylphosphines or Acid Anhydrides thereof The procedures in Examples 1, 2 and 3 may be readily adapted by those of skill in the art of synthetic organic chemistry to any suitably stable polyazamacrocyclic compound. Suitable polyazamacrocyclic compounds include the following triaza and tetraaza macrocyclic compounds available from the Aldrich Chemical Co, Milwaukee, Wis.:

1,5,9-triazacyclododecane (see FIG. 10);
1,4,8,12-tetraazacyclopentadecane (see FIG. 11); and
1,4,8,11-tetraazacyclotetradecane (see FIG. 12).

The following citations are incorporated by reference herein insofar as their pertinence for the reasons cited.

REFERENCES

[1] E. Carafoli and J. T. Penniston, *Sci. Amer.* 253:70 (1985).

[2] R. D. Grubbs and M. E. Maguire, *Magnesium* 6:113 (1983).

[3] G. Charton, G. Rovira, Y. Ben-Ari and V. Leviel, *Exp Brain Res.* 58:202 (1985).

[4] D. Veloso, R. W. Gwynn, M. Oskarsson, and R. L. Veech, *J. Biol Chem* 248:4811 (1973).

[5] J. R. Lopez, L. Alamo, C. Caputo, J. Vergara, and R. Di Polo, *Biochim. Biophys. Acta* 804:1 (1984).

[6] C. H. Fry, *Magnesium* 5:306 (1986).

[7] F. J. Brinkley and A. Scarpa, *FEBS Lett* 50:82 (1975).

[8] T. J. Rink, R. Y. Tsien, and T. Pozzan, *J. Cell. Biol.* 95:189 (1982).

[9] B. E. Corkey, J. Duszynski, T. L. Rich, B. Matschinsky, and J. R. Williamson, *J. Biol. Chem.* 258:14294 (1986).

[10] G. A. Smith, T. R. Hesketh, J. C. Metcalfe, J. Feeney, and P. G. Morris, *Proc. Natl. Acad. Sci. USA* 80:7178 (1983).

[11] J. C. Metcalfe, T. R. Hesketh, and G. A. Smith, *Cell Calcium* 6:183 (1985).

[12] L. A. Levy, E. Murphy, B. Raju, and R. E. London, *Biochemistry* 27:4041 (1988).

[13] E. Murphy, C. Steenbergen, L. A. Levy, B. Raju, and R. E. London, *J. Biol. Chem.* 264: 5622 (1989).

[14] E. Marban, M. Kitakaze, H. Kusuoka, J. K. Poterfield, D. T. Yue, and V. P. Chacko, *Proc. Natl. Acad. Sci. USA* 84:6005 (1987).

[15] H. M. Irving, M. C. Miles, and L. D. Petit, *Anal. Chim. Acta* 38 475 (1967).

[16] M. S. Cacei and W. P. Cacheris, *Byte* 5:340 (1984).

[7] (a) C. F. G. C. Geraldes, A. D. Sherry, and W. P. Cacheris, *Inorg. Chem.* 28:336 (1989). (b) S. Cortes, E. Brucher, C. F. G. C. Geraldes, and A. D. Sherry *Inorg. Chem.* 29:5 (1990).

[18] M. I. Kabachnik, T. Ya. Medved, Yu. M. Polikarpov, B. K. Scherbakov, F. I. Belskii, E. I. Matrosov, and M. P. Pasechnik, *Izv. Akad. Nauk. SSSR Ser Khim* 769 (1984).

[19] R. K. Gupta, J. L. Benovic, and Z. B. Rose, *J. Biol. Chem.* 253:6472 (1978).

[20] P. W. Flatman and V. L. Lew, *Nature* (London) 267:360 (1977).

[21] A. Bevilacqua, R. T. Gelb, W. B. Hobard, and L. F. Zompa, *Inorg. Chem.* 26:2699 (1987).

What is claimed is:

1. A polyazamacrocyclic compound-metal complex having the formula where
x is 2, 3 or a combination of p 2(s) and q 3(s) where p+q=y;
y is 4;
R is $(CH_2)_zP(=O)R^1R^2$;
$R^1$ is $R^3$ or $OR^3$ where $R^3$ is alkyl, cycloalkyl or aryl;
$R^2$ is H or alkyl; and
z is 1 to 3;
r is 2 or 3; and
M is a metal ion.

2. The complex of claim 1 where $M^{+r}$ is $Ca^{+2}$, $Mg^{+2}$, $Zn^{+2}$ or $Gd^{+3}$.

3. A method for enhancing a magnetic resonance image of a subject, the method consisting essentially of administering to the subject a polyazamacrocyclic compound-metal complex having the formula where
x is 2, 3 or a combination of p 2(s) and q 3(s) where p+q=y;
y is 4;
R is $(CH_2)_zP(=O)R^1R^2$;

$R^1$ is $R^3$ or $OR^3$ where $R^3$ is alkyl, cycloalkyl or aryl;
$R^2$ is H or alkyl; and
z is 1 to 3;
M is a paramagnetic metal;
r is 2 or 3; and obtaining a magnetic resonance image of said subject.

4. The method of claim 3 wherein the metal is a lanthanide.

5. The method of claim 3 wherein the metal is gadolinium and r is 3.

* * * * *

UNITED STATES PATENT AND TRADEMARK OFFICE
CERTIFICATE OF CORRECTION

PATENT NO. : 5,342,606

DATED : Aug. 30, 1994

INVENTOR(S) : Sherry et al.

It is certified that error appears in the above-indentified patent and that said Letters Patent is hereby corrected as shown below:

```
At column 15, line 4, please delete "to3;" and insert therefor
-- to 3;--.
```

Signed and Sealed this

Twenty-fifth Day of October, 1994

Attest:

BRUCE LEHMAN

*Attesting Officer*   *Commissioner of Patents and Trademarks*